United States Patent [19]

Schmidt et al.

[11] Patent Number: 4,900,863
[45] Date of Patent: Feb. 13, 1990

[54] PROCESS FOR THE PURIFICATION OF N-ACYLASPARTAME

[75] Inventors: Erwin Schmidt, Kelkheim; Reinhold Keller, Bad Soden am Taunus, both of Fed. Rep. of Germany

[73] Assignee: Hoechst Aktiengesellschaft, Frankfurt am Main, Fed. Rep. of Germany

[21] Appl. No.: 108,954

[22] Filed: Oct. 16, 1987

[30] Foreign Application Priority Data

Oct. 20, 1986 [DE] Fed. Rep. of Germany ....... 3635582

[51] Int. Cl.⁴ .......................................... C07C 101/102
[52] U.S. Cl. ........................................................ 560/41
[58] Field of Search ......................................... 560/41

[56] References Cited

U.S. PATENT DOCUMENTS 4,638,081  1/1987  Elefante ........................... 560/41

FOREIGN PATENT DOCUMENTS 012977   12/1984  European Pat. Off. .............. 560/41
55-167268 12/1980  Japan ..................................... 560/41
61-212597  9/1986  Japan ..................................... 560/41
2140805  12/1984  United Kingdom .................. 560/41

Primary Examiner—Bruce Gray
Attorney, Agent, or Firm—Finnegan, Henderson, Farabow, Garrett and Dunner

[57] ABSTRACT

The α-linked dipeptide formed from aspartic acid and phenylalanine ester can be separated very well from the corresponding β-linked component by recrystallizing the mixture from a buffered, aqueous solution.

7 Claims, No Drawings

PROCESS FOR THE PURIFICATION OF N-ACYLASPARTAME

In order to synthesize the sweetener aspartame, L-asparticanhydride which is protected on the nitrogen atom is reacted with methyl L-phenylalanine to produce an aspartame which is protected on the terminal nitrogen atom, and the protective group is then split off from this aspartame by enzyme action or by hydrogenolysis or hydrolysis.

Suitable protective groups are, in particular, the benzoyl, phenylacetyl, phenoxyacetyl, phenoxypropionyl or benzyloxycarbonyl radical, as listed in German Patent 3,523,018.

The reaction of the protected aspartic anhydride with phenylalanine ester does not, however, take place in a uniform manner. Depending on the reaction conditions and the substituents, considerable amounts of the end product containing a β-linkage are obtained in addition to the α-attachment of the aspartic acid radical (Chemistry and Industry, 15.7.1985, page 485).

In order to remove the undesired β-component, it is suggested in German Offenlegungsschrift 2,053,188 that the α-/β-mixture obtained should not be purified, for example by crystallization, until after the protective group has been split off. However, since aspartame is unstable at fairly high temperatures and forms decomposition products such as diketopiperazines (Food Technology, July 1984, page 53), this process is disadvantageous and, particularly in the case of fairly large batches, is associated with considerable losses.

It therefore seemed advantageous to separate off the β-component before the elimination of the protective group. However, recrystallization from the customary organic solvents has a completely inadequate purifying effect or is associated with high losses.

It has now been found, surprisingly, that the α-linked dipeptide formed from aspartic acid and phenylalanine ester can be separated from the corresponding β-linked component if a mixture of the two components containing acyl protective groups is recrystallized from aqueous, buffered solutions, whereby one of the components remains in solution while the other is precipitated.

The invention therefore relates to a process for the separation of mixtures of compounds of the general formulae I and II

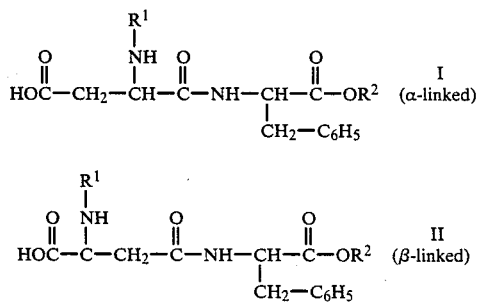

in which $R^1$ denotes an amino protective group and $R^2$ represents an alkyl radical having 1 to 4 carbon atoms, which comprises recrystallizing from aqueous, buffered solutions.

Although the separation process according to the invention is also suitable for mixtures of other N-acylated α-aspartylphenylalanine and β-aspartylphenylalanine esters, it is employed with advantage for the separation of the α-components and β-components of aspartylphenylalanine esters which are protected by N-benzoyl, N-phenylacetyl, N-benzyloxycarbonyl, N-phenoxyacetyl or N-phenoxypropionyl groups, since these esters can be converted into the unprotected aspartame particularly easily by enzyme action, as described in German Patent Application 3,523,018, or by hydrogenolysis as in German Offenlegungsschrift 2,053,188. Furthermore, aliphatic acyl radicals having $C_1$–$C_4$ carbon atoms, such as, for example, formyl, acetyl, propionyl, n-butyryl or isobutyryl, are also preferentially suitable.

The use of the phenylacetyl, phenoxyacetyl or benzyloxycarbonyl protective groups, which can be introduced particularly easily, is particularly advantageous. When the phenoxypropionyl radical is introduced, either a mixture of diastereomers is obtained or it is necessaryy to start from phenoxypropionic acid which is a single enantiomer.

The reaction of the protected aspartic anhydride can be carried out with phenylalanine esters in which the alkoxy radical contains 1 to 4 carbon atoms. For example, the n-, iso- or tert.-butyl, n-propyl, isopropyl, ethyl and methyl esters are suitable. The use of the methyl ester is particularly advantageous, since the sweetener aspartame is obtained directly by this means without further transesterification.

Examples of suitable buffer systems are aqueous solutions of adequately soluble sodium, potassium, ammonium, magnesium or calcium salts of carbonic acid, phosphoric acid or water-soluble carboxylic or phosphonic acids. Suitable ammonium salts are also the salts of organic primary, secondary and tertiary amines and also quaternary ammonium salts or salts of guanidine, biguanide or thiourea.

The buffer systems can be prepared by dissolving the suitable salts individually or as a mixture and also by dissolving the free bases and acids.

The buffer systems can be added in excess, in stoichiometric amounts or in less than equivalent amounts. It is possible to employ any desired excess of the buffer system. However, for economic reasons and in order to obtain α-aspartame free from salts, no advantage is afforded by an excess of more than 2 mol of buffer.

It is particularly advantageous to determine, for example in brief preliminary tests, the amount of buffer which is exactly sufficient to keep in solution the β-alkylaspartame present. The optimum amount and the optimum pH for an individual case must be determined. The pH depends mainly on the solubility of the α-component and the β-component and their salts and on their hydrolysis constants. The pH can also be adjusted by adding to the solution or suspension of the acylaspartame a suitable amount of a base, for example sodium hydroxide solution, aqueous ammonia or an amine. In such cases the acylaspartame itself acts as a buffer component. However, the addition of free alkali metal bases results readily, particularly at fairly high temperatures, in the saponification of the alkyl ester group of the aspartame.

The pH of the aqueous solution can change during the process according to the invention. If, for example, a less than equivalent amount of sodium hydroxide solution is used, the starting pH is 14, and this declines to 4 after the addition of the acrylaspartame. As already indicated, a partial saponification of the methyl ester groups takes place readily within the alkaline range. On the other hand, the purifying effect is considerably less if a phosphate buffer solution having an initial pH of 3 before the addition of the alkylaspartame is used. An optimum separation of the α-component and β-component is obtained in systems in which the pH is 4 to 6 after the addition of the acylaspartame. It is not possible to give an upper limit for the pH of the buffer solution before the addition of the acylaspartame, since, for example, an aqueous solution of potassium carbonate forms potassium hydroxide, with the elimination of carbon dioxide, merely when warmed or when inert gas is passed through it. (Gmelin, System No. 22, K 1936-38, page 822). It is advantageous for the pH of the buffer solution before the addition of the acylaspartame to be between 5 and 12, particularly in order to avoid losses of the methyl ester.

The following are examples of particularly suitable buffer systems:

| | |
|---|---|
| ammonium or alkali metal phosphate buffer: | pH 4 to 7 |
| ammonium or alkali metal citrate buffer: | pH 6.5 |
| ammonium or alkali metal borate buffer: | pH 6.0 |
| alkali metal bicarbonate solution: | pH 8 |
| ammonium or alkali metal carbonate solution: | pH 12 |
| ammonium bicarbonate solution: | pH 7 |

The physiologically harmless and low-cost phosphate buffer, which makes it possible to adjust the pH to any desired figure within wide ranges of concentration, is particularly preferred.

The buffer solutions are prepared in the customary manner, as described, for example, in Küster/Thiel/Fischbeck, Logarithmic Computation Tables, 100th edition, Berlin 1969, pages 263 et seq.

The acylaspartame is recrystallized from an aqueous solution. Depending on the reaction conditions, it can be obtained in the form of the free compound or the anionic constituent of a salt. It can be employed as such without further treatment for the subsequent stages of the synthesis of aspartame. It is also possible, however, to liberate the free acylaspartame by means of acids. It can then be isolated in a solid form or by extraction by means of solvents.

It is not necessary for the purification that the acylaspartame should dissolve completely when the buffer system is heated. On the contrary, the α-component and β-component are also separated if, under suitable conditions, part of the mixture of substances does not dissolve or only melts.

The crystallization can be influenced in an individual case by adding water-miscible solvents. It is also possible to isolate the purification product in a dissolved form by adding solvents of limited miscibility with water before, during or after the recrystallization.

In general, a single recrystallization process is sufficient to obtain α-acylaspartame of a purity considerably higher than 90%. In the case of mixtures having a very high β-content (30–50%), it is advantageous under certain circumstances to repeat the purification process once or several times.

EXAMPLE

The process conditions and the results are shown in the following table.

10 g portions of a 99% α/β-dipeptide mixture are heated for a few minutes in the solvents indicated, in the course of which the crude product either did (yes) or did not (no) dissolve completely. The mixture was then cooled to room temperature and the product was filtered off with suction, rinsed with a little water and dried at 60°.

Analysis:

The α-content and β-content of the products were determined by means of HPLC.
Apparatus: Spark Holland model SpH 126.
Column: VA steel 4.6 mm nominal value: 25 cm long.
UV detector: 254 nm.
Recording: Computing integrator.
Procedure: Isocratic at 40° in a column oven.
for phenylacetylaspartame: mobile phase: acetonitrile containing 2 ml of 85% strength $H_3PO_4$/liter; 70 bar; flow rate 1 ml/minute; dosage 20 ml.
Retention time of the α-component: 5.1 minutes.
Retention time of the β-component: 6.1 minutes.
for benzoxycarbonylaspartame:
Mobile phase: 60% acetonitrile and 40% 0.01 molar aqueous $NaClO_4$ solution; 30 bar; flow rate 1.5 ml/minute; dosage 20 ml.
Retention time of the α-component: 4.7 minutes.
Retention time of the β-component: 8.9 minutes.

TABLE

Weight of sample: in each case 10.0 g of crude product; $R^2 = CH_3$

| crude product | | | completely | purified product | | pH | |
| --- | --- | --- | --- | --- | --- | --- | --- |
| $R^1$ | α-content % | solvent | dissolved | α-content % | α-yield % | before | after |
| | | | | | | solution of the substance | |
| 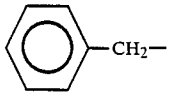 | 81,3 | 100 ml of 0.4 molar Na phosphate buffer solution | yes | 99.5 | 98 | 6.5 | 5 |
| | | 100 ml of 0.25 molar $NaHCO_3$ solution | no | 95 | 45 | 8 | 5 |
| | | 100 ml of 0.07 molar $NaHCO_3$ solution | no | 95 | 97 | 8 | 4 |
| | | 100 ml of 0.025 molar $K_2CO_3$ solution | no | 99 | 75 | 12 | 4 |
| | | 100 ml of 0.5 molar $NH_3$ solution | yes | 100 | 27 | 12 | 6 |
| | | 100 ml of 0.07 molar $NH_3$ solution | no | 90 | 62 | 12 | 4 |
| 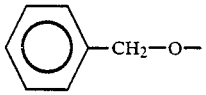 | 83,8 | 100 ml of 0.45 molar K phosphate buffer solution | no | 85 | 92 | 5 | 4 |
| | | | no | 92 | 92 | 6 | 5 |
| | | | yes | 99 | 93 | 7 | 5 |

TABLE -continued

| | crude product | | | completely | purified product | | pH before | after |
| --- | --- | --- | --- | --- | --- | --- | --- | --- |
| $R^1$ | | α-content % | solvent | dissolved | α-content % | α-yield % | solution of the substance | |
| | | | 110 ml of 0.45 molar Na citrate buffer solution | yes | 91 | 99 | 4.5 | 5 |

Weight of sample: in each case 10.0 g of crude product; $R^2 = CH_3$

We claim:

1. A process for the separation of a mixture of compounds of the formulas I and II

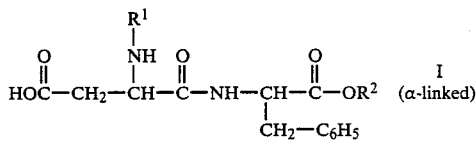

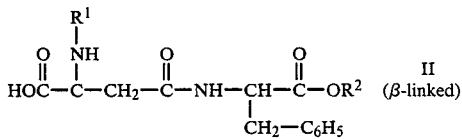

in which $R^1$ denotes an amino protective group and $R^2$ represents an alkyl radical having 1 to 4 carbon atoms, which comprises buffering a mixture of compounds of the formulas I and II to a suitable pH range such that the compounds of one of formulas I and II are at least partially in a solution and the compounds of the other of the formulas are not in the solution, with the proviso that said buffering does not include the use of zinc salts.

2. The process as claimed in claim 1, wherein $R^1$ denotes a benzoyl, phenylacetyl, phenoxyacetyl, phenoxypropionyl or benzyloxycarbonyl group or an aliphatic acyl radical having 1 to 4 carbon atoms.

3. The process as claimed in claim 1, wherein $R^2$ denotes a methyl group.

4. The process as claimed in claim 1, wherein a buffered solution having a pH of 3 to 14 is used.

5. The process as claimed in claim 4, wherein a buffered solution having a pH value of 5 to 12 is used.

6. The process as claimed in claim 1, wherein a solution of ammonium and/or an alkali metal phosphate, citrate, borate, bicarbonate or carbonate is used as the buffer.

7. The process as claimed in claim 6, wherein ammonium and/or an alkali metal phosphate buffer is used.

* * * * *